(12) United States Patent
Perez et al.

(10) Patent No.: US 7,265,259 B2
(45) Date of Patent: Sep. 4, 2007

(54) GSK-3β EXPRESSED IN A TRANSGENIC MOUSE

(75) Inventors: Félix Hernandez Perez, Madrid (ES); Jesús Avila De Grado, Madrid (ES); José Javier Lucas Lozano, Madrid (ES)

(73) Assignees: Consejo Superior de Investigaciones Clentificas, Madrid (ES); Universidad Autonoma de Madrid (UAM), Madrid (ES)

( * ) Notice: Subject to any disclaimer, the term of this patent is extended or adjusted under 35 U.S.C. 154(b) by 281 days.

(21) Appl. No.: 10/276,460

(22) PCT Filed: May 18, 2001

(86) PCT No.: PCT/GB01/02218

§ 371 (c)(1),
(2), (4) Date: May 19, 2003

(87) PCT Pub. No.: WO01/88109

PCT Pub. Date: Nov. 22, 2001

(65) Prior Publication Data

US 2003/0177510 A1 Sep. 18, 2003

(30) Foreign Application Priority Data

May 18, 2000 (GB) .................... 0012056.8

(51) Int. Cl.
*A01K 67/033* (2006.01)
*A01K 67/027* (2006.01)
*G01N 33/00* (2006.01)
*C12N 15/00* (2006.01)

(52) U.S. Cl. .................. 800/18; 800/3; 800/9; 800/12; 800/25

(58) Field of Classification Search .............. 800/3, 800/12, 13, 14, 18, 9, 25
See application file for complete search history.

(56) References Cited

FOREIGN PATENT DOCUMENTS

| WO | WO95/05466 | 2/1995 |
|----|-----------|--------|
| WO | WO98/03644 | * 1/1998 |
| WO | WO 01/02552 | 1/2001 |

OTHER PUBLICATIONS

Ristevsk, S. Making Better Transgenic Models. Molecular Biotechnology. 2005, vol. 29, pp. 153-163.i.*
Montoliu, L. Gene Transfer Strategies in Animal Transgenesis. Cloning and Stem Cells. 2002, vol. 4, No. 1, pp. 39-46.*
Echeverria et al. Rat Transgenic Models with a Phenotype of Intracellular A-Beta Accumulation in Hippocampus and Cortex. J. Alzheimer's Dis. 2004, vol. 6, pp. 209-219.*
Gingrich and Roder, "Inducible Gene Expression in the Nervous System of Transgenic Mice" *Annu. Rev. Neurosci.* 21:377-405, 1998.
Nagai et al., "Rats Expressing Human Cytosolic Copper-Zinc Superoxide Dismutase Transgenes with Amyotrophic Lateral Sclerosis: Associated Mutations Develop Motor Neuron Disease" *J. Neurosci.* 21:9246-9254, 2001.
Si-Hoe et al., "Production of Transgenic Rodents by the Microinjection of Cloned DNA into Fertilized One-cell Eggs" *Mol. Biotechno.* 17:151-82, 2001 (Abstract only).
Ripps et al., "Transgenic mice expressing an altered murine superoxide dismutase gene provide an animal model of amyotrophic lateral sclerosis" *Proc. Natl Acad Sci USA* 92:689-693, 1995.
Gordon et al., "Genetic transformation of mouse embryos by microinjection of purified DNA" *Proc Natl Acad Sci* USA 77:7380-7384, 1980.
Brownlees et al. (1997) "Tau Phosphorylation in Transgenic Mice Expressing Glycogen Syntheses Kinase—3Beta Transgenes," Neuro report, Rapid Communications of Oxford 8(15):3251-3255.
Mayford et al. (1996) "Control of Memory Formation Through Regulated Expression of a CAMKII transgene" Science 274:1678-1683.
Lucas et al. (2001) "Decreased Nuclear B-Catenin, Tau Hyperphosphorylation and Neurodigeneration in GSK-3B Conditional Transgenic Mice" EMBO J. 20(1/2):27-39.
Baron et al. (1995) "Co-Regulation of Two-Gene Activities by Tetracycline via a bidirectional promoter", Nucleic Acid Res. 23(17):3605-3606.
Ishiguro et al. (1993) "Glycogen synthesis kinase 3 Beta is identical to tau protein kinase I generating several epitopes of paired helical filaments" FEBS 6 letters 325(3):167-172.

* cited by examiner

*Primary Examiner*—Deborah Crouch
(74) *Attorney, Agent, or Firm*—Fish & Richardson P.C.

(57) ABSTRACT

A transgenic animal in which GSK-3β protein is overexpressed is useful as a model for neurodegenerative disease.

8 Claims, 7 Drawing Sheets

GSK-3β EXPRESSED IN A TRANSGENIC MOUSE

CROSS-REFERENCE TO RELATED APPLICATIONS

Figure 1:
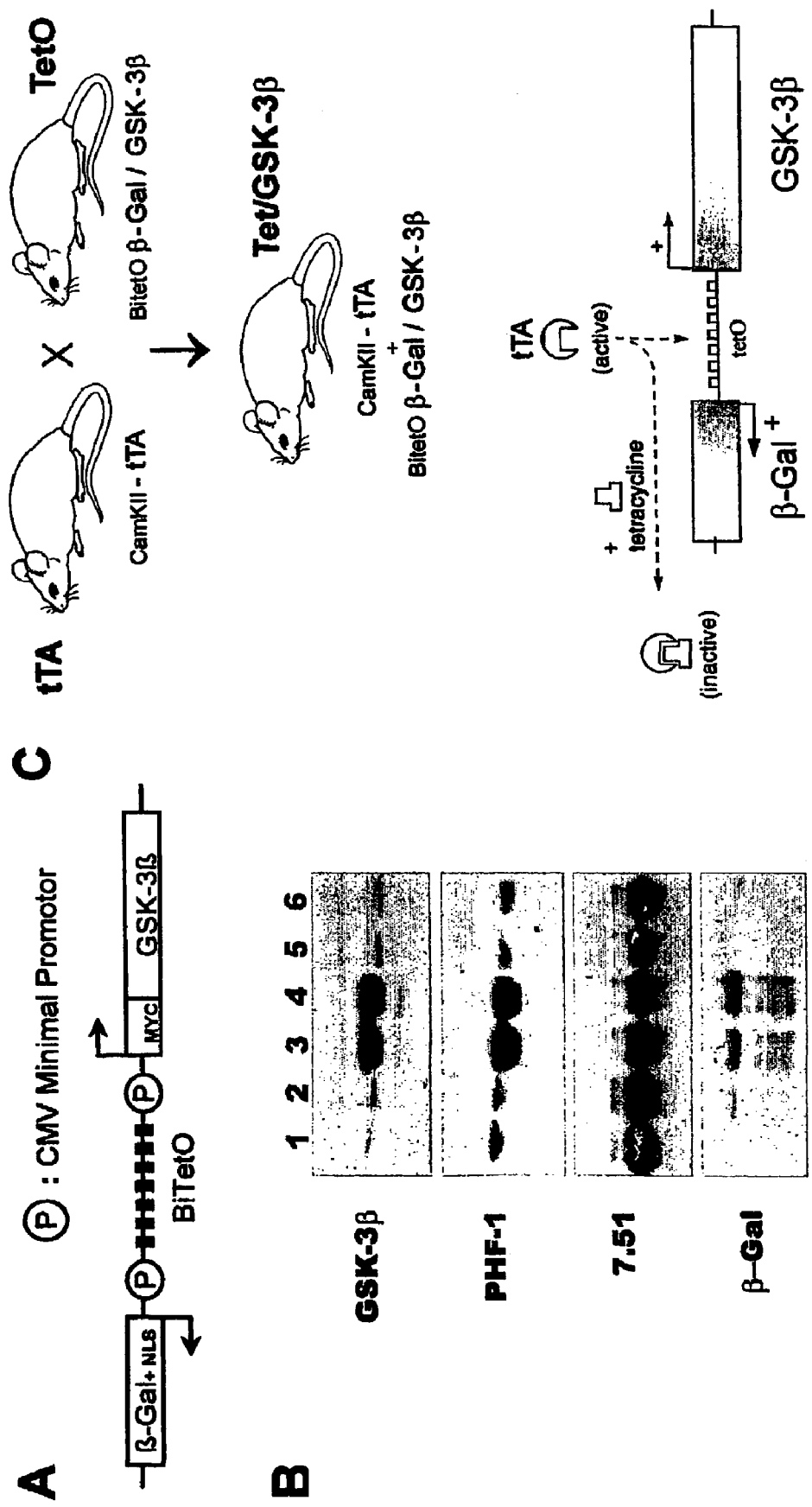

This application is the National Stage of International Application No. PCT/GB01/02218 filed on May 18, 2001, which claims priority from United Kingdom Patent Application No. GB0012056.8, filed on May 18, 2000. Both prior applications are incorporated herein by reference in their entirety.

The present invention relates to animal models for neurodegenerative disease, in particular for Alzheimer's disease.

BACKGROUND OF THE INVENTION

Alzheimer's disease, (AD), is the most common neurodegenerative disease in developed countries, and is characterized by progressive memory loss and impairments in language and behavior that ultimately lead to death (Alzheimer, 1911; Yankner, 1996). The cognitive decline in AD is accompanied by neuronal atrophy and loss mainly in cortex, hippocampus, and amygdala (Gomez-Isla et al., 1997). In addition to a specific pattern of neuronal cell death, AD is characterized by two neuropathological hallmarks, senile plaques and neurofibrillary tangles (NFTs).

Senile plaques are extracellular deposits of amyloid fibrils made of the 39-43 amino acid β-amyloid peptide (AB) often surrounded by dystrophic neurites (Glenner and Wong, 1984; Masters et al., 1985; Selkoe, 1994).

NFTs are intraneuronally generated aggregates of paired helical filaments (PHFs) which are assembled from hyperphosphorylated forms of the microtubule-associated protein tau (Greenberg et al., 1992; Grundke-Iqbal et al., 1986; Lee et al., 1991; Morishima-Kawashima et al., 1995). NFTs can be found in all brain regions undergoing degeneration in AD and their spatio-temporal pattern of appearance correlates well with that of cell death and symptomatology (Arriagada et al., 1992; Braak and Braak, 1991; Gomez-Isla et al., 1997).

Molecular insights into AD pathogenesis have arisen from genetic studies in families affected by inherited forms of AD (FAD). These account for only a small percentage of AD cases but have allowed the identification of mutations in three different genes that are responsible for triggering the disease. These genes are the presenilins-1 and -2 (PS-1 and PS-2) and the amyloid precursor protein (APP) (Hardy, 1996). Mutations in APP result in increased production of Aβ (Price and Sisodia, 1998) while PS-1 and PS-2 mutations favor processing of APP into the long and most amyloidogenic form of Aβ ($A\beta_{42}$) (Citron et al., 1997; Duff et al., 1996; Price and Sisodia, 1998; Scheuner et al., 1996). This genetic evidence together with in vitro and in vivo studies of Aβ induced neurotoxicity point to Aβ formation and/or aggregation as a key event in triggering AD.

Little is known about downstream intracellular effectors that account for neuronal dysfunction, although activation of glycogen synthase kinase-3β (GSK-3β) has been proposed. GSK-3β is a proline directed serine/threonine kinase that was originally identified due to its role in glycogen metabolism regulation and that is most abundant in the CNS (Woodgett, 1990). Apart from being implicated in insulin and IGF-1 mediated signal transduction, GSK-3β is also involved in the wnt/wingless signaling pathway as the key enzyme regulating β-catenin stability and, as a consequence, its translocation to the nucleus and its transcriptional activity (Anderton, 1999; Earth et al., 1997).

GSK-3β is one of the best candidate enzymes for generating the hyperphosphorylated tau that is characteristic of PHFs (Lovestone and Reynolds, 1997). GSK-3β can be purified from microtubules (Ishiguro et al., 1988) and has been shown to phosphorylate tau in most sites hyperphosphorylated in PHFs both in transfected cells (Lovestone et al., 1994) and in vivo (Hong et al., 1997; Munoz-Montano et al., 1997). Furthermore, GSK-3β accumulates in the cytoplasm of pretangle neurons and its distribution in brains staged for AD neurofibrillary changes is coincident with the sequence of development of these changes (Pei et al., 1999; Shiurba et al., 1996).

Exposure of cortical and hippocampal primary neuronal cultures to Aβ has been shown to induce activation of GSK-3β (Takashima et al., 1996), tau hyperphosphorylation (Busciglio et al., 1995; Ferreira et al., 1997; Takashima et al., 1998), and cell death (Busciglio et al., 1995; Estus et al., 1997; Forloni et al., 1993; Loo et al., 1993; Pike et al., 1991; Takashima et al., 1993). Blockade of GSK-3β expression or activity, either by antisense oligonucleotides or by lithium, prevents Aβ induced neurodegeneration of cortical and hippocampal primary cultures (Alvarez et al., 1999; Takashima et al., 1993).

PS-1 has been shown to directly bind GSK-3β and tau in coimmunoprecipitation experiments from human brain samples (Takashima et al., 1998). Thus, the ability of PS-1 to bring GSK-3β and tau into close proximity suggests that PS-1 may regulate phosphorylation of tau by GSK-3β. Mutant forms of PS-1 in transfection experiments result in increased PS-1/GSK-3β association and increased phosphorylation of tau (Takashima et al., 1998). Furthermore, PS-1 has also been shown to form a complex with the GSK-3β substrate β-catenin in transfected cells (Murayama et al., 1998; Yu et f al., 1998) and in vivo Yu et al., 1998; Zhang et al., 1998) and this interaction increases β-catenin stability (Zhang et al., 1998). Pathogenic PS-1 mutations reduce the ability of PS-1 to stabilize β-catenin, which in turn results in decreased β-catenin levels in AD patients with PS-1 mutations (Zhang et al., 1998).

OBJECT OF THIS INVENTION

There is a need for animal models which closely mimic the pathology of neurodegenerative diseases such as AD, which are vital for the understanding of the disease and testing of new therapies.

The present invention sets out to approach this problem of animal models.

SUMMARY OF THE INVENTION

The invention provides a transgenic animal model for Alzheimer's disease, wherein GSK-3β protein is over-expressed in the animal.

PREFERRED EMBODIMENTS

In particular, the invention provides a transgenic animal model, wherein expression of the GSK-3β protein is conditional.

Preferably GSK-3β is the only enzyme which is over-expressed, and indeed it is more preferred that GSK-3β is the only protein which is over-expressed. Overexpression of the GSK-3β protein alone surprisingly produces a pathology in the transgenic animal that closely mimics AD. Specifically, GSK-3β overexpression results in decreased levels of nuclear β-catenin, increased phosphorylation of tau protein, neuronal cell death, reactive astrocytosis and microgliosis. The similar pathology of the transgenic model and the natural disease state makes the model of the present invention highly valuable for disease analysis.

Preferably the animal used in the transgenic studies is a mammal, such as a mouse, rat or primate. Other suitable animals for use in transgenic studies are well known in the art.

The present invention also extends to the methods used for production of the transgenic animal.

The animal model of the invention is useful in the testing of new drugs or therapies to treat neurodegenerative diseases such as AD. Therefore the invention extends to a method of identification of a therapy useful in the treatment of AD, comprising administering the therapy to the transgenic animal of the invention and monitoring for an effect on pathology or behaviour.

DETAILED EMBODIMENTS OF THE INVENTION

For preference we employ a tet-regulated system in mice. The tet-regulated system has been used for conditional gene expression in eukaryotic cell systems and mice (Gingrich and Roder, 1998). By using this system to drive transgenic expression of a mutated form of huntingtin, some of us have recently generated the first conditional animal model of a neurodegenerative disease (Yamamoto et al., 2000). The tet-regulated system can be particularly useful when mimicking pathological conditions since it may be used to circumvent perinatal lethality due to toxicity of the transgene, trigger expression of the transgene only in adult life, and stop transgene expression once relevant phenotypic changes have taken place (Kelz et al., 1999; Yamamoto et al., 2000).

Regulation of the system is achieved through the tetracycline-regulated transactivator (tTA), a chimeric protein comprised of the tet-repressor DNA-binding domain and the VP16 trans activation domain (Gossen and Bujard, 1992). This protein binds specifically to the tetO operator sequence and induces transcription from an adjacent CMV minimal promoter. The combination of both tTA and the tetO elements thus allows for continual transactivation of a given transgene. Tetracycline and its analogues can bind to tTA. When this happens, tTA is prevented from binding to tetO, and transcription is inhibited.

In this way, we have produced conditional transgenic mice overexpressing GSK-3β in the brain during adulthood while avoiding perinatal lethality due to embryonic transgene expression. These mice show destabilization of β-catenin and hyperphosphorylation of tau in hippocampal neurons, the latter resulting in pretangle-like somatodendritic localization of tau. Neurons displaying somatodendritic localization of tau often show abnormal morphologies and detachment from surrounding neuropil. Reactive astrocytosis and microgliosis were indicative of neuronal stress and death. This finding was further confirmed by TUNEL staining of dentate gyrus granule cells. Overexpression of GSK-3β in cortex and hippocampus leads to decreased levels of nuclear β-catenin, increased phosphorylation of tau in AD relevant epitopes, neuronal cell death, and reactive astrocytosis and microgliosis. Our results therefore demonstrate that in vivo overexpression of GSK-3β results in neurodegeneration and suggest that these mice can be used as an animal model to study the relevance of GSK-3β deregulation to the pathogenesis of Alzheimer's disease.

EXAMPLE

The present invention is further illustrated by the following example of our experimental work.

Generation of Injection Fragment

An 8.0 kb Ase I fragment (BitetO) was used for microinjection. To generate BitetO, a 1.5 kb Hind III fragment corresponding to Xenopus GSK-3B cDNA with an N-terminal MYC epitope was excised from a pcDNA3-GSK3 plasmid (Sanchez et al., 2000). This fragment was subcloned into the pCRII cloning vector (Invitrogen) digested with Hind III. The correct orientation was tested for by Xho I digestion. A 1.5 kb fragment was then excised by Nsi I-Not I digestion and subcloned into the Pst I-Not I sites of a plasmid containing a bidirectional tetO sequence flanked by cytomegalovirus (CMV) minimal promotors with lacZ reporter sequences (pBI-3, (Baron et al., 1995)). Lastly, the 8.0 kb Ase I BitetO fragment was microinjected into single-cell CBAxC57BL/6 embryos. Founder mice were identified by PCR and confirmed by Southern analysis. Founder mice were then crossed with wild type CBAxC57BL/6 mice and Southern analysis was performed on F1 progeny to test for multiple insertion events of the microinjection freagment. All mice reported here resulted from a single integration event (data not shown).

COS Cell Transfections

COS-7 cells were maintained in Dulbecco's modified essential medium (DMEM; Gibco BRL) supplemented with 10% (v/v) fetal bovine serum, 2 mM glutamine, 100 units ml$^{-1}$ penicillin and 100 µg ml$^{-1}$ streptomycin and incubated in 95% air/5% CO2 in a humidified incubator at 37° C. Cells at 50-70% confluency in 35 mm diameters dishes were transiently transfected with LipofectAMINE (Gibco BRL)/5 µg of DNA according to the manufacturer's recommendations. Cells were harvested and analysed 48 h following transfection.

Animals

Mice were bred at the Centro de Biologia Molecular "Severo Ochoa" animal facility. Mice were housed 4 per cage with food and water available ad libitum and maintained in a temperature-controlled environment on a 12/12 hour light-dark cycle with light onset at 07:00 hours.

Antibodies

The following anti-tau antibodies were used: 7.51 (Novak et al., 1991) (a kind gift of Dr. C. Wischik, MRC, Cambridge, UK), PHF-1 (Greenberg et al., 1992; Otvos et al., 1994) (a kind gift of Dr. P. Davies, Albert Einstein Coll., Bronx, N.Y., USA), 12E8 (Seubert et al., 1995) (a kind gift of dr. P. Seubert, Athena, San Francisco, Calif., USA), AD2 (Buee-Scherrer et al., 1996) (a kind gift of Dr. C. Mourton-Gilles, Montpellier, France). According to the residue numbering of the longest human tau isoform of 441 amino acids (Goedert et al., 1989), antibody 12E8 reacts with tau when serine 262 is phosphorylated (Seubert et al., 1995). Antibodies PHF-1 and AD2 recognize tau when serines 396 and 404 are phosphorylated (Buee-Scherrer et al., 1996; Otvos et al., 1994). Other monoclonal antibodies were: anti-GSK3-β Transduction Laboratories), anti-β-catenin (Transduction Laboratories), anti-β-tubulin (Sigma), anti-β-galactosidase (Promega), anti-myc (Developmental Studies Hybridoma Bank, Iowa, USA), anti-GFAP (PharMingen, Calif., USA), OX42 (a kind gift of Dra. P. Bovolenta, Instituto Cajal, Spain), EDI (Serotec; UK). Antibody raised against the nuclear protein U"snRNP was kindly donated by Dr. J. Ortin (CNB, Madrid, Spain).

Immunohistochemistry

Mice were deeply anesthetized with pentothal and transcardially perfused with 4% paraformaldehyde in 0.1 M phosphate buffer during 10 min. The brains were postfixed in 4% paraformaldehyde for two hours at room temperature and placed in 30% sucrose in PBS for 48 hours at 4° C. Sagittal sections (30 µm) were cut in a freezing microtome and collected in PBS. Free floating sections were pretreated with 0.3% $H_2O_2$ in PBS and incubated overnight at 4° C. with primary antibodies: PHF-1 (1/150), AD-2 (1/2000), anti-myc (1/20), anti-GSK-3β (1/500), anti-β-galactosidase (1/5000), anti-GFAP (1/250), OX42 (1/1000) in PBS containing 0.2% Triton X-100, 10% normal goat serum (GmCO) and 1% BSA (Boehringer-Mannheim). Following three PBS washes, sections were carried through standard avidin-biotin immunohistochemical protocols using an Elite Vectastain kit (Vector Laboratories). Chromogen reaction was performed with diaminobenzidine (Sigma) and 0.003% $H_2O_2$ for ten minutes. The sections were mounted on chromalum-coated slides and coverslipped with Aqua-Poly-Mount (Polysciences). Omission of the primary antibody resulted in absence of labeling.

LacZ Staining

LacZ staining was performed as follows. Fresh frozen sections were postfixed for 10 minutes in 4% paraformaldehyde in Soren's buffer. Slides were then incubated for 1 hour at 30° C. in lacZ staining solution (1 mg/ml X-gal (4-chloro-5-bromo-3-indolyl-β-galactosidase, Boehringer Mannheim), 5 mM potassium ferrocyanide, 5 mM potassium ferricyanide and 2 mM $MgCl_2$ in PBS). After staining, sections were rinsed and dry-mounted.

Tunel Assay

The DNA fragmentation characteristic of apoptosis was detected by TUNEL method in paraformaldehyde postfixed brains. The TUNEL staining of vibratome sections was performed by following manufacturer's instructions (In situ Cell Death Detection, POD; Boehringer Mannheim). Treatment with Dnase I was used as a positive control.

Subcellular Fractionation

To prepare membrane and cytosolic extracts, tissues were washed with ice-cold phosphate-buffered saline and homogenized in a hypotonic buffer (0.25 M sucrose, 20 mM HEPES pH 7.4, 2 mM EGTA, 1 mM PMSF, 10 µg/ml aprotinin, 10 µg/ml leupeptine and 10 µg/ml pepstatine). The homogenate (Total cellular fraction) was clarified by centrifugation at 850×g for 15 min at 4° C.; the resulting supernatant was then centrifuged at 100.000×g for 1 h at 4° C. to isolate the membrane fraction as a pellet and the cytoplasmatic fraction as the supernatant.

Brain nuclei were sedimented through a 2 M sucrose cushion. Brain areas from three animals were homogenized in 0.32 M sucrose, 10 mM Tris-HCl pH 7.4, 3 mM $MgCl_2$, 1 mM DTT, 0.1% Triton X-100, 10 µg/ml aprotinin, 10 g/ml leupeptine and 10 µg/ml pepstatin by using a Potter homogenizer provided with a loosely fitting Teflon pestle. The homogenate was filtered through cheese-cloth and centrifuged for 10 min at 1000×g. The pellet was resuspended in 3 ml of homogenization medium without Triton and supplemented with 1.9 M sucrose. This preparation was layered over a cushion of 2M sucrose (10 ml) and centrifuged at 12,000×g in a HB4 rotor (Sorvall). The pellet was resuspended in 0.5 ml of 0.32 M sucrose. The purity of brain nuclei was assessed by light microscopy after crystal violet staining. In addittion, U2snRNP, a known nuclear protein, was used as a nuclear marker in Western blot analysis.

Western Blot Analysis

Brains were quickly dissected on an ice-cold plate. Extracts for Western blot analysis were prepared by homogenizing the brain areas in ice-cold extraction buffer consisting of 20 mM HEPES, pH 7.4, 100 mM NaCl, 20 mM NaP, 1% Triton X-100, 1 mM sodium orthovanadate, 5 mM EDTA, and protease inhibitors (2 mM PMSF, 10 µg/ml aprotinin, 10 µg/ml leupeptin and 10 µg/ml pepstatin). The samples were homogenized and centrifuged at 15,000 g for 20 min at 4° C. The resulting supernatant was collected, and protein content was determined by Bradford. Thirty micrograms of total protein was electrophoresed on 10% sodium dodecyl sulfate-polyacrylamide gel and transferred to a nitrocellulose membrane (Schleicher and Schuell). The experiments were performed using the followed primary monoclonal antibodies: anti-GSK3β (1/2000), PHF-1 (1/200), AD2 (1/2000), 12E8 (1/200), 7.51 (1/100), anti-MYC (1/100), anti-β-tubulin (1/5000), anti-β-galactosidase (1/5000). The filters were incubated with the antibody at 4° C. overnight in 5% nonfat dried milk. A secondary goat anti-mouse antibody (1/5000; Gmco) and ECL detection reagents (Amersham) were used for immunodetection. Quantitation of immunoreactivity was performed by densitometric scanning. Statistical analysis was performed using Student's t test.

Tissue Processing for Electron Microscopy

For electron microscopy, vibratome sections were used. Once immunostained, the sections were post fixed in 2% $OsO_4$ for 1 h, dehydrated, embedded in araldite and flat-mounted in Formvar coated slides, using plastic cover-slips. After polymerization, selected areas were photographed, trimmed, re-embeded in araldite and re-sectioned at 1 µm. These semithin sections were re-photographed and resectioned in ultrathin sections. The ultrathin sections were observed in a Jeol electron microscope, without heavy metal staining to avoid artifactual precipitates.

FIGURES

FIG. 1. Mouse design. A, schematic representation of the BitetO construct. This consists of seven copies of the palindromic tet operator sequence flanked by two CMV promoter sequences in divergent orientations. This bi-directional promoter is followed by a GSK-3β cDNA sequence (encoding a MYC epitope at its 5'end) in one direction and β-galactosidase (LacZ) sequence including a nuclear localization signal (NLS) in the other. B, COS cells were co-transfected with the plasmid containing the BitetO construct and an expression vector coding for human tau (lanes 1 to 6), a third plasmid that allows expression of tTA was added (lanes 3 to 6) either in the absence (lanes 3 and 4) or in the presence (lanes 5 and 6) of 1 µg/ml tetracycline in the culture medium. Protein extracts were probed with antibodies against GSK-3β, AD-like phosphorylated tau (PHF-1), total tau (7.51) and β-galactosidase (β-Gal). C, Tet/GSK-3β mice are generated by crossing mice expressing tTA under control of the CarnKIIa promoter (tTA) with mice that have incorporated the BitetO construct in their genome (TetO). The double transgenic progeny (Tet/GSK-3β) are expected to express GSK-3β constitutively in the brain unless tetracycline or analogs are given orally thus preventing transactivation by tTA.

Figure 2:
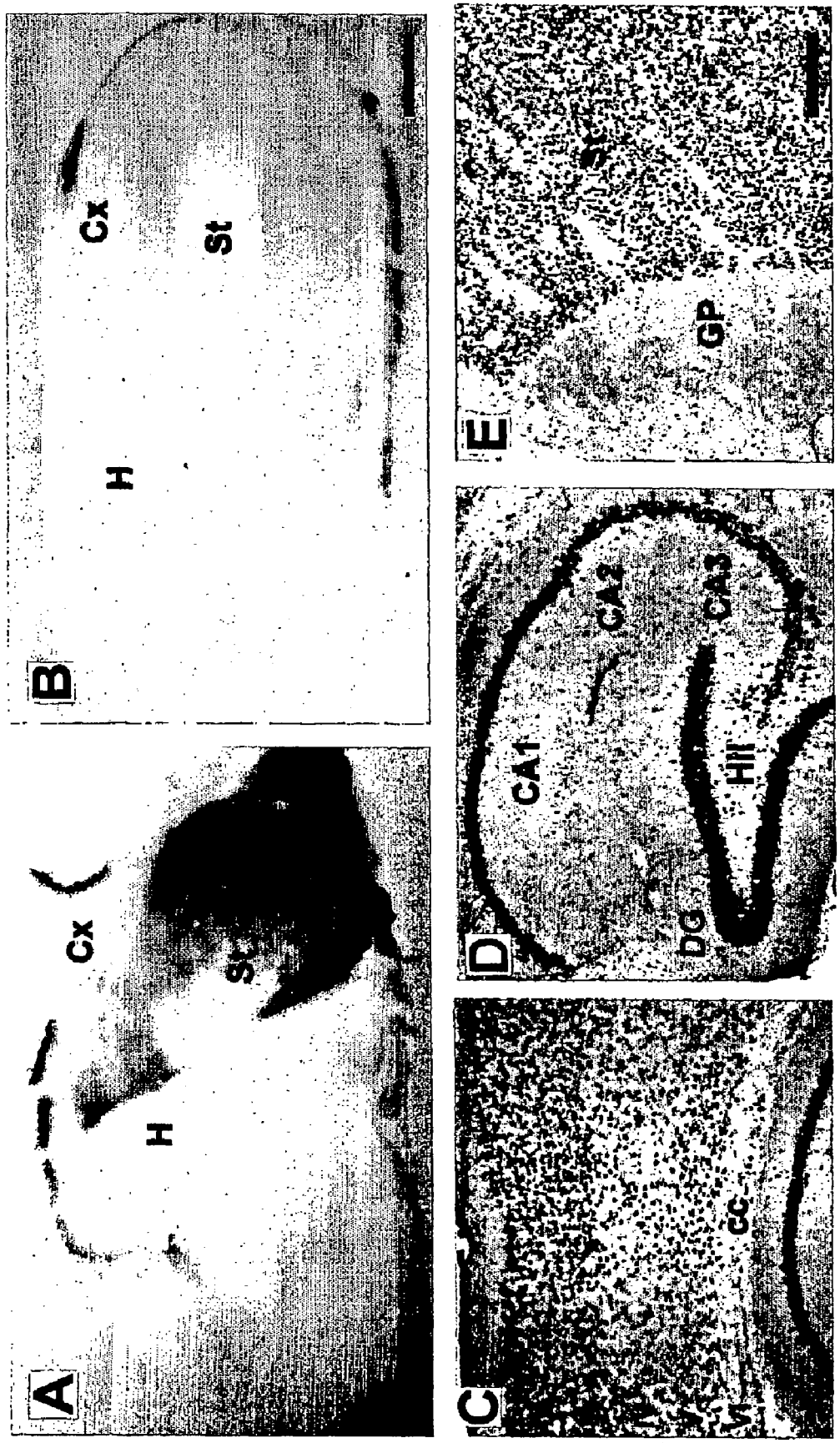

FIG. 2. Pattern of transgene expression in Tet/GSK-3β mice. A-B, X-gal staining of brain sagittal sections from P0

Tet/GSK-3β mice that were either drug-naive (A) or born after giving doxycycline to the mother for five days immediately prior to birth (B). C-E, β-galactosidase immunohistochemistry in sagittal sections of adult (3 months) Tet/GSK-3β mouse brain reveals expression in the different neuronal layers of the cortex (C), the hippocampus (D), and in the striatum (E). H, hippocampus; Cx, cortex; St, striatum; 11-VI, cortical layers; cc, corpus callosum; DG, dentate gyrus, Hil; hillus; GP, globus pallidus. Scale bar in B corresponds to 1 mm in A-B. Scale bar in E corresponds to 200 μm in C-E.

Figure 3:
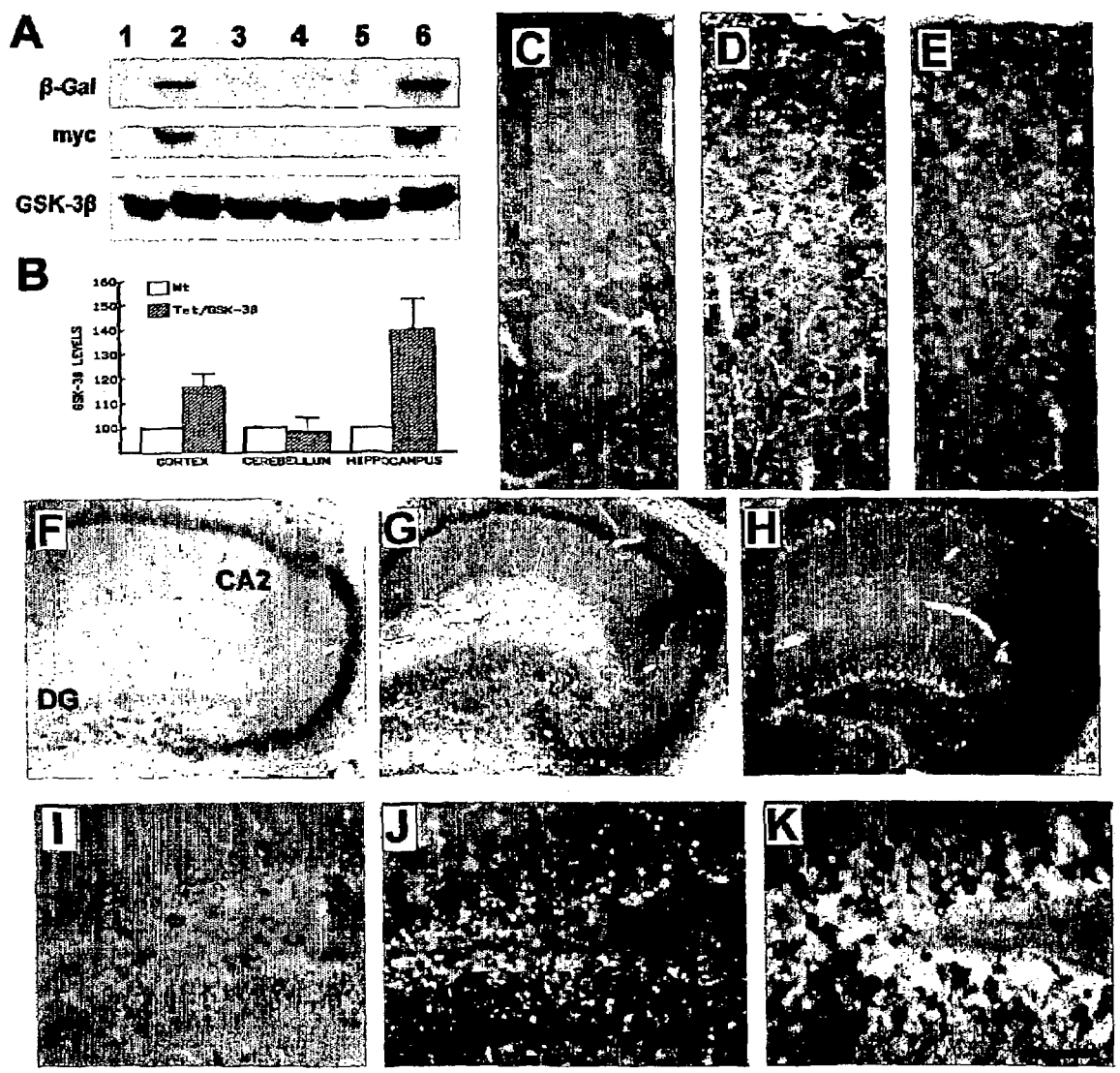

FIG. 3. Overexpression of GSK-3B in cortex and hippocampus of Tet/GSK-3B mice. A, Western blot of protein extracts from cortex (lanes 1 and 2), cerebellum (lanes 3 and 4), and hippocampus (lanes 5 and 6) of wild type (lanes 1, 3, and 5) or Tet/GSK-3β (lanes 2, 4, and 6) mice. B, histogram showing percent increase of GSK-3β levels in Tet/GSK-3β mice. C-E, immunohistochemistry in cortical sections of wild type (C) or Tet/GSK-3β (D and E) mice; performed with antibodies against GSK-3B (C and D) or MYC (E). F-H, immunohistochemistry in hippocampal sections of wild type (F) or Tet/GSK-3β (G and H) mice; performed with an antibody against GSK-3β (F and G) or MYC (H). I-K, high power magnification of the dentate gyri shown in F-H. Scale bar corresponds to 100 μm in C-E, 200 μm in F-H, 60 μm in I-I, and 40 μm in K.

Figure 4:
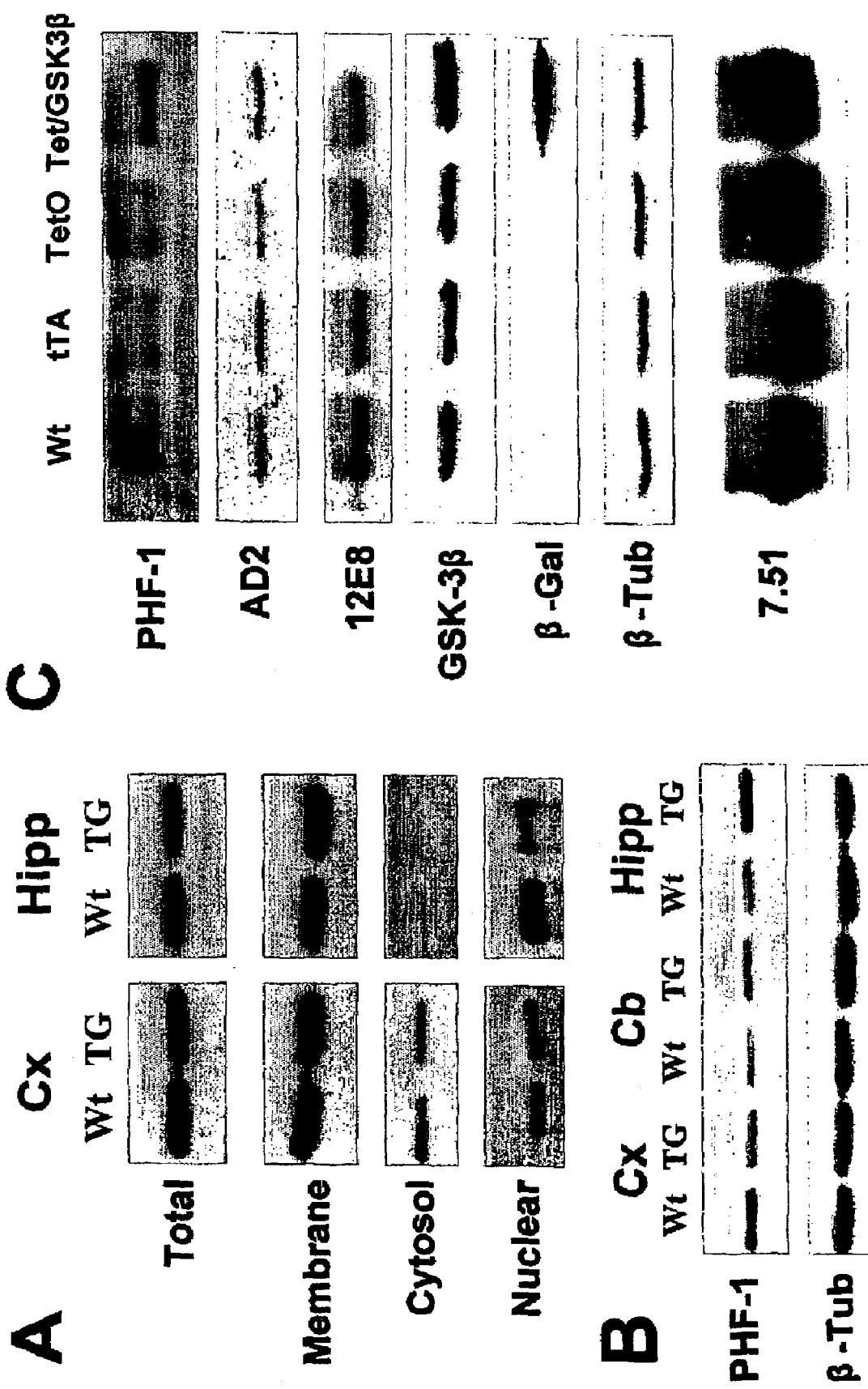

FIG. 4. Effect of GSK-3β overexpression on β-catenin levels and tau phosphorylation. A, Western blot of total cellular, membrane, cytosolic and nuclear preparations from cortex (Cx) and hippocampus (Hipp) of wild type (Wt) or T et/GSK-3β (TG) mice probed with anti-β-catenin antibody. B, Western blot of protein extracts from cortex (Cx), cerebellum (Cb), and hippocampus (Hipp) of wild type (Wt) or Tet/GSK-3β (TG) mice probed with PHF-1 and β-Tubulin antibodies. C, Western blot of hippocampal extracts from wild type (Wt), tTA, TetO, or Tet/GSK-3β mice probed with the indicated antibodies.

Figure 5:
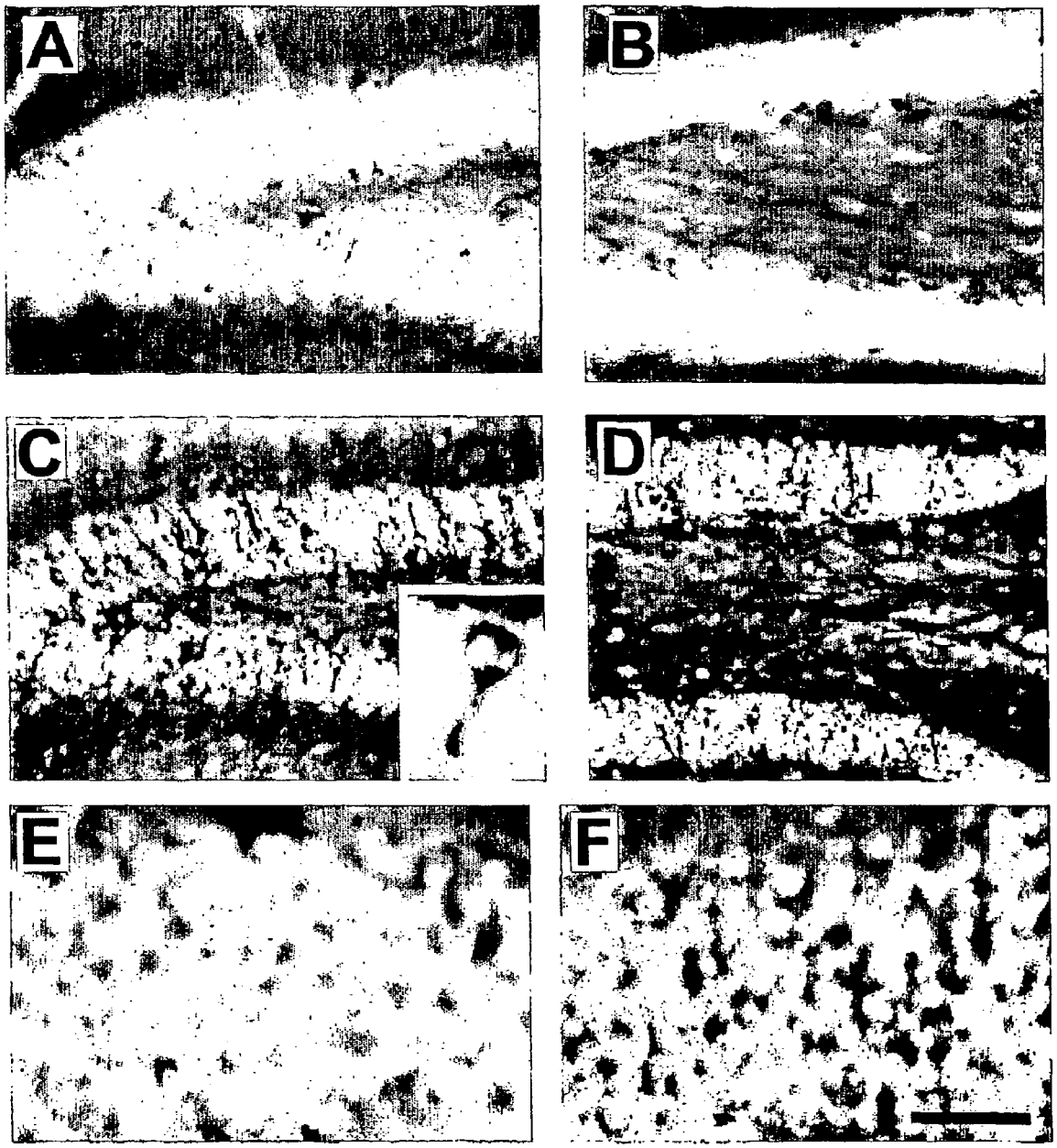

FIG. 5. Somatodendtitic localization of tau in Tet/GSK-3β mice. A-D, PHF-1 immunohistochemistry in the dentate gyrus of wild type (A and B) or Tet/GSK-3β (C and D) mice. E-F, immunohistochemistry performed with 7.51 antibody in the dentate gyrus of wild type (E) or Tet/GSK-3β (F) mice. Arrow in B indicates faintly stained mossy fibers. Inset in C shows higher magnification of a PHF-1 immunostained granule cell. Scale bar corresponds to 200 μm in A-D, and 60 μm in E-F.

Figure 6:
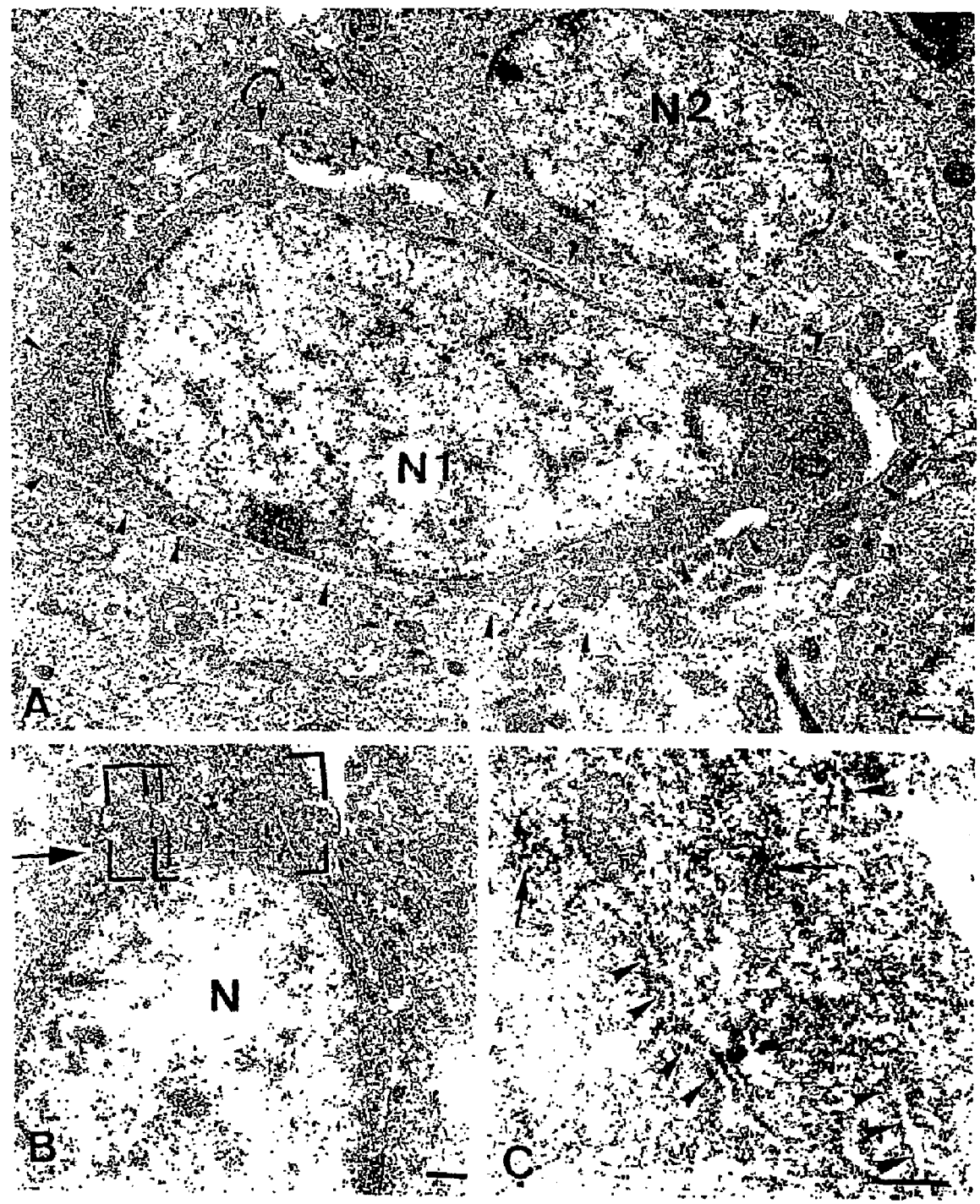

FIG. 6. Electron microscopy study of PHF-1 positive neurons. A, Electron micrograph of two neurons from the dentate gyrus of Tet/GSK-3β mouse hippocampus. N1: Nucleus of a PHF-I immunopositive neuron exhibiting most of its perimeter detached from the surrounding neuropil (arrowheads), in addition to diffi1se cytoplasmic immunostaining. N2: nucleus of a PHF-1 immunonegative neuron. B, Another PHF-1 immunopositive neuron from the dentate gyrus of the same mouse of 4A showing PHF-1 reaction product in patches and associated with rough endoplasmic reticulum. N Unlabeled nucleus. C, High magnification of the framed portion in FIG. 4B, showing the patches of reaction product (arrows) and the labeling of the rough endoplasmic reticulum. No heavy metal staining was performed. Calibration bar corresponds to 0.5 μm in all panels.

Figure 7:
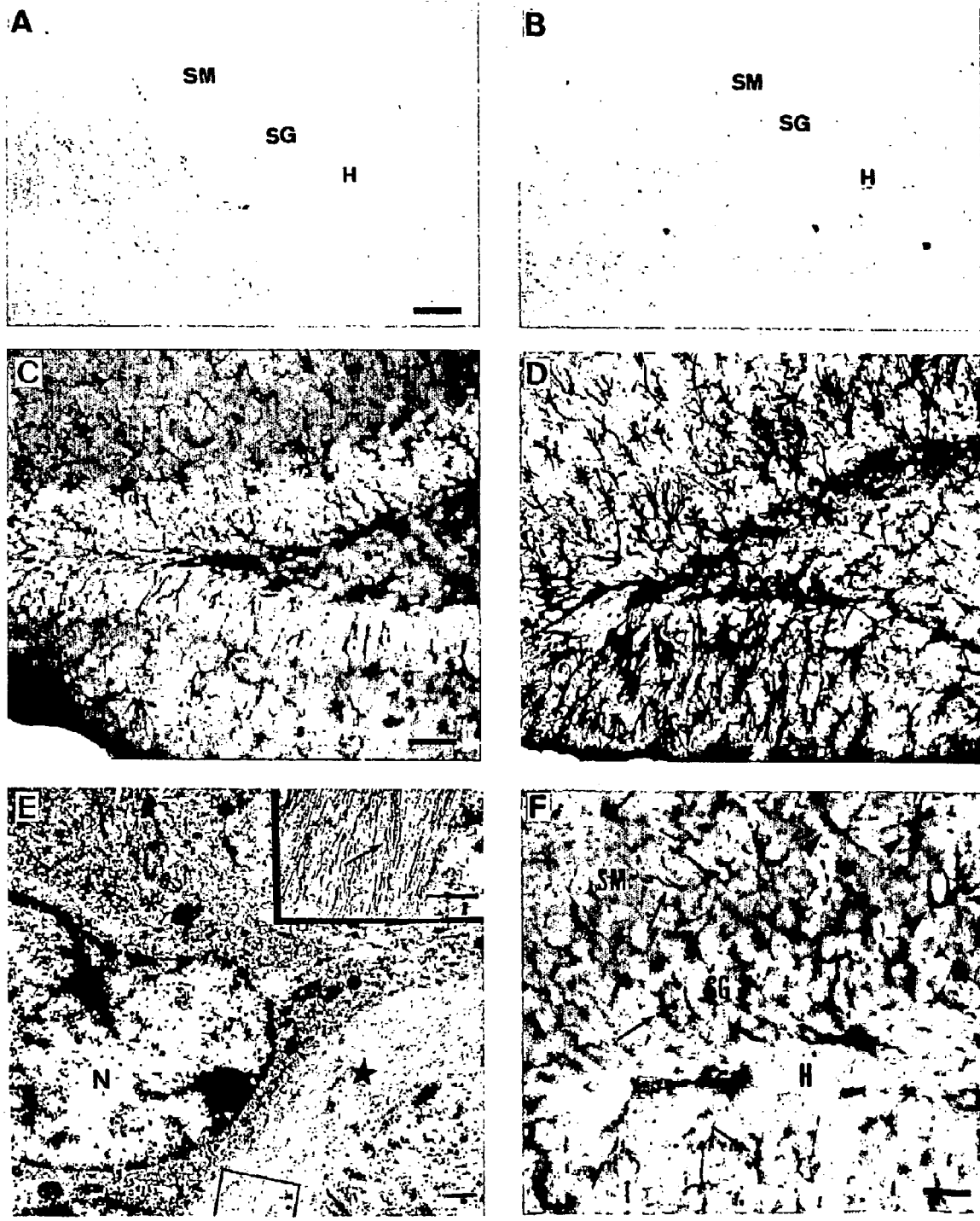

FIG. 7. Neuronal death and reactive gliosis in Tet/GSK-3β mice. A-B, TUNEL staining of the dentate gyrus of wild type (A) or Tet/GSK-3β (B) mice. Arrows indicate TUNEL positive nuclei. C-D, GFAP immunohistochemistry in the dentate gyrus of wild type (C) or Tet/GSK-3β (D) mice. E, electron micrograph of the dentate gyrus of Tet/GSK-3β mouse hippocampus showing a hypertrophic astrocytic process surrounding a PHF-1 immunostained neuron. N: nucleus. Asterisk: diffuse cytoplasmic immunostaining. Black star: hypertrophic astrocytic process. Inset: high magnification of the astrocytic process showing characteristic bundles of glial intermidiate filaments. F, OX-42 immunostaining of the dentate gyrus of a Tet/GSK-3β mouse. Arrows indicate fine immunoreactive microglial processes. Arrowheads indicate immunostained reactive cell bodies. SM, stratum moleculare; SG stratum granulare; H, hillus. Scale bars correspond to 50 μm in A-B, 60 μm in C-D, 0.5 μm in E, and 30 μm in F.

MOUSE CONSTRUCT

We generated a plasmid (Biteto) carrying the bi-directional tet responsive promoter (Baron et al., 1995) followed by both a GSK-3β cDNA (encoding a MYC epitope at its 5' terminus) in one direction and, in the other direction, a cDNA encoding β-galactosidase (β-gal) fused to a nuclear localization signal (FIG. 1A). This plasmid was assayed in transfection experiments performed in COS cells (FIG. 1B). This plasmid by itself or cotransfected with an expression vector coding for tau (FIG. 1B, lanes 1 and 2) had no effect on GSK-3β levels as evidenced by Western blot with an antibody against GSK-3β. When cotransfected with a plasmid that allows expression of tTA (FIG. 1B, lanes 3 and 4) a marked increase in GSK-3β levels was evident. This resulted in increased phosphorylation of tau as evidenced by Western blot with the PHF-1 antibody that recognizes a PHF tau phosphorylation epitope. When tetracycline was present (FIG. 1B, lanes 5 and 6), trans activation of GSK-3β was abolished. These experiments therefore demonstrate conditional expression of GSK-3β from the BitetO construct (FIG. 1A).

The BitetO construct was then microinjected into oocytes and the five resulting transgenic mouse lines were generically designated TetO (FIG. 1C). In the tTA mouse lines, the tTA transgene is under the control of the Calciumlcalmodulin kinase lIa promoter (CamKlIa-tTA lines E and B) (Mayford et al., 1996). These tTA lines were chosen to allow for restricted, conditional expression in the CNS, with particularly high expression in the forebrain (Mayford et al., 1996; Yamamoto et al., 2000). When the TetO mice are crossed with tTA mice, the resulting double transgenic progeny (designated Tet/GSK-3β) are expected to constitutively express both transgenes (FIG. 1C). This expression however can be abolished in the presence of tetracycline or its analogues.

Our previous experience in generating conditional transgenic mice with the tet-regulated system indicates that the genomic site of insertion and/or copy number of the tetO construct influences the final pattern and level of transactivation by tTA. The β-Gal reporter sequence in the BitetO construct permits quick analysis of the pattern of transgene expression in the double transgenic mice either by X-Gal staining or by immunohistochemistry against β-Gal, and furthermore, allows for testing the efficacy of transgene silencing by tetracycline. We took advantage of this to decide which TetO mouse lines were more suitable for our study.

Characterization of Different Tet/GSK-3β Mouse Lines

When the five TetO lines were bred with tTA lines, three of them showed β-Gal expression only in the striatum (data not shown). The two remaining TetO lines (lines G6 and G7) were specially suitable for our study since they exhibited high levels of transgene expression in brain regions relevant to AD such as cortex and hippocampus and we have therefore focused the rest of the study on lines G6 and G7. These two lines transactivate β-Gal in a spatial pattern very similar to that of endogenous CamKIIcα, with expression evident in cortex, hippocampus, striatum and amygdala (FIG. 2). Immunohistochemistry in brain sections of adult Tet/GSK-3β mice shows β-Gal expression in the different neuronal layers of the cortex, the different fields of the hippocampus (including subiculum, CA1, CA2, CA3, and dentate gyrus), and in the 1.1 striatum (FIGS. 2C-E). No β-Gal expression was detected in other brain regions such as globus pallidus, thalamus, brainstem and cerebellum (FIGS. 2A, 2E, 3A, and not shown). A similar pattern and level of transgenic expression was obtained when either CamKIIα-tTA line (E or B) was combined with one TetO line (G6 or G7). In this study we have used each combination interchangeably and thus henceforth we will use the terms tTA and TetO for single transgenic mice, and Tet/GSK-3B for the double transgenic animals.

Tet/GSK-3B mice were viable and fertile and appeared normal without pharmacological intervention to suppress transgene expression. This seemed to contradict the previously postulated toxicity of increased GSK-3β expression in brain (Brownlees et al., 1997). However, heterozygote crosses between tTA and TetO mice did not yield the expected frequency of 25% for each genotype (wild type, tTA, TetO, and Tet/GSK-3β). The Tet/GSK-3β mice were underrepresented (14%, n=401). This might be indicative of lethality due to embryonic overexpression of GSK-3β in Tet/GSK-3β mice.

We had previously observed perinatal transgene expression and lethality in our CamKIIα-tTA driven animal model of Huntington's disease (HD94) (Yamamoto et al., 2000). In the case of HD94 mice, if pregnant mice are given the tetracycline analog doxycycline (2 mg/ml) in the drinking water ad libitum from E15 to birth, only postnatal transgenic expression takes place and the frequency of the four expected genotypes is restored to 25%. We thus decided to apply the same program of perinatal doxycycline treatment to the Tet/GSK-3B mice. We found that at P0, non treated mice show X-gal staining in the forebrain while staining was absent in treated mice (FIGS. 2A and B). This demonstrates that transgene expression in Tet/GSK-3β mice begins during embryonic life and that can be inhibited with doxycycline. As expected, prenatal doxycycline treatment normalized to 25% the frequency of Tet/GSK-3β mice and thus, to maximize yield of double transgenic mice in litters, the perinatal doxycycline treatment was routinely employed.

Tet/GSK-3β mice overexpress GSK-3β in cortex and hippocampus. We then confirmed by Western blot analysis that the brain regions that show β-Gal expression also display increased levels of GSK-3β. Probing protein extracts with an anti-MYC antibody demonstrated that the highest level of transgenic GSK-3β expression takes place in the hippocampus, followed by the cortex (FIG. 3A) while little expression could be detected in the striatum (not shown). Accordingly, probing extracts from 3 month old mice with an antibody raised against GSK-3β (FIGS. 3A and B) we observed a significant ($p<0.02$) 40+/−12.4% increase in GSK-3β levels in the hippocampus of Tet/GSK-3β mice with respect to wild type mice. Cortical extracts also showed increased (17+/−5%) levels of GSK-3β in Tet/GSK-3β mice. No differences in GSK-3β levels were found in the striatum (not shown) or in non forebrain regions such as cerebellum (FIG. 3B). We then monitored at ages ranging from 1 to 12 months the increase in GSK-3β that takes place in the hippocampus and cortex of Tet/GSK-3β mice. The level of overexpression was similar at all tested ages (not shown) and the rest of expreiments in the present study were performed on adult mice at ages between 2.5 and 6 months.

To gain insight into which cell populations are overexpressing GSK-3β, we performed immunohistochemistry with both anti-MYC and anti-GSK-3β antibodies. In the cortex, increased immunoreactivity (IR) for GSK-3β was found in layer II and III pyramidal cortical neurons (FIGS. 3C-E) and in lamina VI neurons adjacent to the corpus callosum (not shown).

In the hippocampus, overexpression of GSK-3β was evident in all regions (subiculum, CA1, CA2, CA3, and dentate gyrus) with the dentate gyrus and CA2 displaying the most prevalent increase (FIGS. 3F-H). The dentate gyrus of wild type mice showed very weak IR for GSK-3β (FIGS. 3F and 3I) while every neuron in the dentate gyrus of Tet/GSK-3β mice overexpressed GSK-3β (FIGS. 3G and 3I). Some of these neurons showed a remarkably high staining with both anti-GSK-3β and anti-MYC antibodies (FIGS. 3I-K) and often exhibited abnormal morphologies such as shrunk cell bodies (not shown). In CA2 pyramidal neurons, a prominent staining in both cell bodies and dendrites was seen in Tet/GSK-3β mice (FIGS. 3G-H).

We next analyzed by Western blot, the effect of GSK-3β overexpression on its AD related substrates β-catenin and tau. β-catenin is a component of cell-cell adherent junctions but also associates with HMG-box transcription factors of the Tcf/LEF family and promotes transcription of target genes. GSK-3β is the key enzyme regulating β-catenin stabilization and subsequent nuclear translocation (Anderton, 1999; Barth et al., 1997).

We first analyzed the levels of β-catenin in total cortical and hippocampal extracts (FIG. 4A). No differences were found between wild type and Tet/GSK-3β mice. We then analyzed β-catenin levels in different cellular compartments. As can be seen in FIG. 4A, no changes were observed in β-catenin levels in membrane or cytosolic extracts from either cortex or hippocampus. When nuclear extracts were analyzed, no significant differences were observed in β-catenin levels in cortex. However, in hippocampus, we observed a significant ($p<0.05$, n=6) 35+/−8% reduction in nuclear β-catenin levels of Tet/GSK-3~mice compared to wild type littermates. This decrease in nuclear β-catenin was also evident by immuno-electron microscopy in the dentate gyrus of Tet/GSK-3β mice (not shown).

We next performed Western blots with tau antibodies in those brain regions which show MYC expression (cortex, striatum, and hippocampus) as well as in the cerebellum. Only the hippocampus showed increased levels of tau phosphorylation as detected by the PHF-1 antibody (FIG. 4B and not shown). The increase in AD-like phosphorylation of tau detected with the PHF-1 antibody was reproduced using the AD2 antibody raised against the same phosphoepitope of tau (FIG. 4C). The increase in PHF-1 and AD2 IR in Tet/GSK-3β mice is not due to altered levels of total tau since no increase was observed with the phosphorylation independent tau antibody 7.51 that recognizes all tau isoforms. Furthermore, phosphorylation at serine 262 which is not adjacent to a proline residue and which has been shown to be independent of GSK-3β in vivo (Munoz-Montano et al., 1997) is not affected in Tet/GSK-3β mice as detected by the 12E8 antibody (FIG. 4C).

We compared tau phosphorylation and transgenic protein expression in the four possible genotypes (wild type, tTA, TetO, and Tet/GSK-3β) (FIG. 4C). Only Tet/GSK-3β mice showed β-Gal expression and increased levels of GSK-3β, and PHF-1 and AD2 tau, therefore demonstrating that transgenic expression and subsequent effects in Tet/GSK-3β mice were due to transactivation by tTA of the BitetO construct and not due to leakage of the latter in the TetO mice.

Somatodendritic Localization of AD-Like Hyperphosphorylated Tau

We analyzed by immunohistochemistry which hippocampal neuronal populations exhibit the increase in PHF-1 IR observed by Western blot. Increased PHF-1, immunostaining was most evident in the dentate gyrus (FIG. 5). In wild type mice, granule cells of the dentate gyrus show no detectable PHF-1 IR (FIG. 5A), although some staining could be detected in the mossy fibers projecting to CA3 (FIG. 5B). Tet/GSK-3B mice show a marked increase in the staining of mossy fibers (FIG. 5D) and, interestingly, most granule cells show strong somatodendritic PHF-1 immunostaining, thus resembling the pretangle stage of AD neurofibrillary degeneration (FIG. 5C).

Phosphorylation of tau by GSK-3β decreases the affinity of tau for microtubules in vitro and in transfected cells (Lovestone et al., 1996). This may explain in part the somatodendritic staining found with the PHF-1 antibody. To test this, we performed immunohistochemistry with 7.51, an antibody raised against the tubulin binding domain of tau and that therefore recognizes tau only when it is not bound to microtubules. Interestingly, the 7.51 antibody stained somas of Tet/GSK-3β but not wild type dentate gyrus granule cells (FIG. 5F). The morphology of 7.51 stained cells was very similar to that observed with PHF-1 antibody (see inset in FIG. 5C).

Strong somatodendritic immunostaining of hyperphosphorylated tau may also be indicative of aberrant aggregated forms of tau such as PHFs. Thioflavine-S staining in AD brains reveals both neurofibrillary tangles and amyloid plaques. We therefore performed Thioflavine-S staining in brain sections of Tet/GSK-3β mice. No Thioflavine-S fluorescence was detected, either in the granule cells of the dentate gyrus or in any other brain region, indicating the absence of PHF bundles and of β-sheet protein aggregates. The lack of Thioflavine-S fluorescence could still be compatible with the existence of few, short PHFs, thus representing initial steps of neurofibrillary degeneration.

To analyze this possibility, we then studied by electron microscopy Tet/GSK-3β granule cells since they show strong somatodendritic immunolabeling for PHF-1. A diffuse reaction product was present in the perikaryon of these neurons (FIGS. 6A-C), although in some cases we also observed patches of dark reaction product (FIG. 6C). However, PHFs were not observed either in the dark reaction product patches or in other portion of the diffuse immunolabeled cytoplasm. Interestingly, immunolabeled material was often seen along the cytoplasmic face of the rough endoplasmic reticulum (RER) cisternae, and the above mentioned dark stained patches were, in some occasions, in close proximity of these labeled RER cisternae (FIG. 6C). Interestingly, Tet/GSK-3β neurons with diffuse PHF-1 cytoplasmic labeling very frequently appeared detached from the surrounding neuropil, showing a widened extracellular space along most of their periphery (FIG. 6A) whereas unlabeled neurons did not show any detachment. We also observed no detachment of granule cell neurons of wild type mice.

Neuronal Cell Death and Reactive Gliosis in the Hippocampus of Tet/GSK-3β Mice

Previous studies have demonstrated that GSK-3B is inhibited by the PI 3-kinase/PKB survival pathway which prevents apoptosis (Cross et al., 1995; Cross et al., 1994; Hurel et al., 1996; Saito et al., 1994). This, together with the observation that destabilization of β-catenin by mutations in PS-1 potentiate neuronal apoptosis (Zhang et at., 1998), prompted us to explore whether apoptosis was taking place in Tet/GSK-3β mice as a consequence of the overexpression of GSK-3β.

Different neuronal populations of Tet/GSK-3β mice showed TUNEL labeling that was absent in wild type mice. This was observed mainly in the granule cells of the dentate, gyrus (up to 5 labeled granule cells per 30 µm section of Tet/GSK-3β dentate gyrus versus no labeling in wild type dentate gyrus. FIGS. 4A and B). Some TUNEL positive cells were also observed adjacent to the corpus callosum in cortical lamina VI of Tet/GSK-3β mice (not shown).

We next tested whether the neuronal alterations and/or death triggered by overexpression of GSK-3β in Tet/GSK-3β mice was accompanied by glial alterations such as reactive astrocytosis and microgliosis. Immunohistochemistry performed with an antibody raised against glial fibrillary acidic protein (GF AP) revealed reactive astrocytosis in different brain regions. Coincident with TUNEL labeling, GF AP staining was most prevalent in the dentate gyrus and in deep cortical layers (FIGS. 7C and D, and not shown). Electron microscopy studies confirmed the presence of highly activated astrocytic processes, full of glial intermediate filaments, in the dentate gyrus of the Tet/GSK-3β mice. These were often found surrounding PHF-1 IR neurons (FIG. 7E).

To test whether microgliosis was taking place in the hippocampus of Tet/GSK-3β mice we performed immunohistochemistry with OX42, LN-3, and ED1 antibodies. Similar results were obtained with all of these three antibodies (FIG. 7F shows OX-42 immunohistochemistry). When compared to wild type hippocampal sections, an increase in fine microglial processes was found in the stratum granulare of Tet/GSK-3β mice. Furthermore immunostained cell bodies corresponding to reactive microglia were found only in Tet/GSK-3β mice, mainly in the stratum moleculare of the hippocampus (arrowheads in 7F).

DISCUSSION

By using a conditional transgenic approach here we show that in vivo overexpression of GSK-3β results in neurodegeneration. Conditional transgenic mice overexpressing GSK-3β also mimic different biochemical and cellular aspects of AD such as B-catenin destabilization and pretangle-like somatodendritic localization of hyperphosphorylated tau. Our results therefore support the hypothesis that deregulation of GSK-3β might be a critical event in the pathogenesis of AD and raise the possibility that these mice may serve as a useful animal model to study some aspects of this pathology.

GSK-3β is active during animal development as a component of the Wnt signaling pathway and plays an important role in cell-fate decisions and pattern formation (Bourouis et al., 1990; Ruel et al., 1993; Siegfried et al., 1992; Siegfried et al., 1994). Accordingly, the ability of lithium to inhibit GSK-3B has been suggested to account for its teratogenic effects (Klein and Melton, 1996; Stambolic et al., 1996). Apart from their well established roles in early development, Wnt signaling and GSK-3β have been-shown to participate in postnatal cerebellar granule cell synaptogenesis (Hall et al., 2000; Lucas and Salinas, 1997). Toxicity of GSK-3β overexpression during embryonic and postnatal development of the CNS may explain why Brownlees and collaborators were unable to generate transgenic mice with detectable overexpression of GSK-3β even with neuronal specific promoters. This prompted these authors to suggest the use of tightly controlled inducible expression systems (Brownlees et al., 1997). In our case, we also find that a fraction of double transgenic mice die perinatally and that this can be rescued by silencing transgene expression during embryonic life. However, some mice can survive without pharmacological intervention. There are at least two reasons why this may happen. First, the promoter that we use (CamKIIα) has a more restricted pattern of expression than the one employed by Brownilees and collaborators (NF-L). Second, in our binary system the transgene by itself is silent. This avoids lethality of founders due to the toxicity of the transgene. Subsequent breeding with tTA mice allows to select those double transgenic descendants with a genetic background permissive for the embryonic overexpression of the transgene.

Somatodendritic accumulation of hyperphosphorylated tau is an early event in the evolution of AD neurofibrillary degeneration (Braak et al., 1994). Pretangle-like immunostaining of tau is found in transgenic mice overexpressing different isoforms of tau (Brion et al., 1999; Gotz et al., 1995; Ishihara et al., 1999; Spittaels et al., 1999). Somatodendritic localization of tau in these mice might be due to saturation of the tau binding capacity of microtubules. The excess of tau is then susceptible to accumulate in soma and undergo ulterior modifications such as phosphorylation and conformational changes. In Tet/GSK-3β mice, hyperphosphorylation and somatodendritic localization of tau take place without affecting the total level of tau, therefore, in closer resemblance to the situation found in AD and other taupathies. According to the increase in 7.51 immunostaining found in Tet/GSK-3β mice and to previous in vitro studies (Novak et al., 1991), increased tau phosphorylation in Tet/GSK-3β mice most likely leads to a decreased affinity of tau for microtubules and subsequent accumulation of the protein in the soma.

We find that somatodendritic tau in Tet/GSK-3β mice is often associated with the endoplasmic reticulum. Similar results were found in transgenic mice overexpressing the shortest isoform of tau (Brion et al., 1999) and in aged sheep (Nelson et al., 1993). In all of these cases, immunodetection was performed with antibodies that recognize phosphorylation or conformation epitopes found in PHF-tau. Interestingly, PHFs in AD brains are often found arising from the endoplasmic reticulum and other membrane structures (Gray et al., 1987; Metuzals et al., 1988; Papasozomenos, 1989). It is therefore possible that, in animal models, association of tau with the endoplasmic reticulum represents an early stage in the formation of neurofibrillary lesions. An additional and compatible explanation for the association of tau with the endoplasmic reticulum might be its interaction with PS-1. PS-1 has been found to bind both tau and GSK-3β in co-immunoprecipitation experiments performed on human brain extracts (Takashima et al., 1998), and PS-1 is located predominantly in the endoplasmic reticulum and in the Golgi apparatus (Selkoe, 1998).

Several mechanisms may account for the neuronal stress and death (revealed by staining of reactive glia and TUNEL) detected in Tet/GSK-3β mice. In view of the effects of GSK-3β overexpression on tau phosphorylation and compartmentalization, a possible mechanism could be the disorganization of the microtubule cytoskeleton. In this case, as a consequence of a diminished stabilization of microtubules by tau, a decrease in microtubule content similar to that found in AD brains (Terry, 1998) would be expected in Tet/GSK-3β mice. Additionally, GSK-3β is negatively regulated by the survival pathway involving PI-3 kinase (Cross et al., 1995; Cross et al., 1994; Hurel et al., 1996; Saito et al., 1994) and challenging cultured cortical neurons with trophic factor withdrawal or with PI-3 kinase inhibitors leads to stimulation of GSK-3β that results in apoptosis (Hetman et al., 2000; Pap and Cooper, 1998). Finally, decreased β-catenin mediated transcription has been shown to potentiate neuronal apoptosis in primary neuronal cultures exposed to β-amyloid (Zhang et al., 1998) or transfected with mutant PS-1 (Weihl et al., 1999). Little is known about the target genes transactivated by β-catenin which are responsible for the increased susceptibility to apoptosis. Tet/GSK-3β mice can be a useful system to identify such genes by differential display or DNA-micro array approaches.

Substantial progress has been made during the last few years towards the generation of transgenic mouse models of AD, particularly in regard to the β-amyloid toxic cascade and plaque formation (Price and Sisodia, 1998). Sequential improvements have been achieved by generating mice with higher expression levels of mutated forms of APP and by breeding them with mutant PS-1 transgenic mice that favor APP processing into Aβ42 (Guenette and Tanzi, 1999). However, if GSK-3β deregulation is a key event in the pathogenesis of AD, Tet/GSK-3β mice may constitute an alternative and/or complementary mouse model of AD.

Most of the effort made to date in transgenic models of AD has focused on mimicking the neuropathological hallmarks of AD. This may require excessively artificial modifications to reproduce within the life-span of a mouse, something that is formed over many years in a human. Alternatively, it may simply not be possible to mimick all aspects of AD neuropathology in mice because it requires human specific clues (as is the case for β-amyloid induced toxicity in vivo (Geula et al., 1998). GSK-3β is an enzyme found at the convergence of the pathways involved in AD-like tau hyperphosphorylation, β-amyloid induced toxicity and PS-1 mutations. When compared to already existing mouse models of AD, Tet/GSK-3β mice are unique in the sense that they reproduce downstream intraneuronal dysfunction that may be ultimately responsible for some aspects of AD. A prediction of this hypothesis would be that GSK-3β levels (or activity) and substrates should be found altered in AD patients. Evidence in favor of this has already been reported (Pei et al., 1999; Shiurba et al., 1996).

Neurodegeneration in Tet/GSK-3β mice is in good agreement with the neuroprotective effect of lithium, a relatively specific GSK-3β inhibitor. The neuroprotective effects of lithium have been ascribed to its ability to inhibit GSK-3β (Alvarez et al., 1999; Hetman et al., 2000) and to upregulate Bcl-2 (Chen et al., 1999) and downregulate Bax proteins (Chen and Chuang, 1999) in neurons (Revised in Manji et al, 1999]. Tet/GSK-3β, mice are thus a good tool to test the neuroprotective effect of forthcoming GSK-3β specific inhibitors. Furthermore, their efficacy can be compared with the effect of silencing transgene expression by administering tetracycline analogs.

REFERENCES

Alvarez, G., Munoz-Montano, I. R., Satrustegui, I., Avila, I., Bogonez, E., and Diaz-Nido, I. (1999). Lithium protects cultured neurons against beta-amyloid-induced neurodegeneration. FEBS Lett 453, 260-4.

Alzheimer, A. (1911). Über eigernartige krankhertsfülle des späteren alters. z. Ges. Neurol. Psychiat. 4,356-385.

Anderton, B. H. (1999). Alzheimer's disease: clues from flies and worms. Curr Biol 9, R106-9.

Arriagada, P. V., Growdon, J. H., Hedley-Whyte, E. T., and Hyman, B. T. (1992). Neurofibrillary tangles but not senile plaques parallel duration and severity of Alzheimer's disease. Neurology 42,631-9.

Baron, U., Freundlieb, S., Gossen, M., and Bujard, H. (1995). Co-regulation of two gene activities by tetracycline via a bidirectional promoter. Nucleic Acids Res 23, 3605-6.

Barth, A. I., Nathke, I. S., and Nelson, W. J. (1997). Cadherins, catenins and APC protein: interplay between cytoskeletal complexes and signaling pathways. Curr Opin Cell Bio 19, 683-90.

Bourouis, M., Moore, P., Ruel, L., Grau, Y., Heitzler, P., and Simpson, P. (1990). An early embryonic product of the gene shaggy encodes a serine/threonine protein kinase related to the CDC28/cdc2+ subfamily. Embo 19, 2877-84.

Braak, E., Braak, H., and Mandelkow, E. M. (1994). A sequence of cytoskeleton changes related to the formation of neurofibrillary tangles and neuropil threads. Acta Neuropathol 87, 554-67.

Braak, H., and Braak, E. (1991). Neuropathological stageing of Alzheimer-related changes. Acta Neuropatho 182, 239-59.

Brion, J. P., Tremp, G., and Octave, J. N. (1999). Transgenic expression of the shortest human tau affects its compartmentalization and its phosphorylation as in the pretangle stage of Alzheimer's disease [see comments]. Am J. Pathol 154, 255-70.

Brownlees, J., Irving, N. G., Brion, J. P., Gibb, B. J., Wagner, U., Woodgett, J., and Miller, C. C. (1997). Tau phosphorylation in transgenic mice expressing glycogen synthase kinase-3beta transgenes. Neuroreport 8, 3251-5.

Buee-Scheffer, V., Condamines, O., Mourton-Gilles, C., Lakes, R., Goedert, M., Pau, B., and Delacourte, A. (1996). AD2, a phosphorylation-dependent monoclonal antibody directed against tau proteins found in Alzheimer's disease. Brain Res Mol Brain Res 39, 79-88.

Busciglio, J., Lorenzo, A., Yeh, J., and Yankner, B. A. (1995). beta-amyloid fibrils induce tau phosphorylation and loss of microtubule binding. Neuron 14, 879-88.

Chen, G., Zeng, W. Z., Yuan, P. X., Huang, L. D., Jiang, Y. M., Zhao, Z. H., and Manji, H. K. (1999). The mood-stabilizing agents lithium and valproate robustly increase the levels of the neuroprotective protein bcl-2 in the CNS. J Neurochem 72, 879-82.

Chen, R. W., and Chuang, D. M. (1999). Long term lithium treatment suppresses p53 and Bax expression but increases Bcl-2 expression. A prominent role in neuroprotection against excitotoxicity. J Biol Chem 274, 6039-42.

Citron, M., Westaway, D., Xia, W., Carlson, G., Diehl, T., Levesque, G., Johnson-Wood, K., Lee, M., Seubert, P., Davis, A., Kholodenko, D., Motter, R., Sherrington, R., Perry, B., Yao, H., Strome, R., Lieberburg, I., Rommens, J., Kim, S., Schenk, D., Fraser, P., St George Hyslop, P., and Selkoe, D. J. (1997). Mutant presenilins of Alzheimer's disease increase production of 42-residue amyloid beta-protein in both transfected cells and transgenic mice [see comments]. Nat Med 3, 67-72.

Cross, D. A., Alessi, D. R., Cohen, P., Andjelkovich, M., and Hemrnings, B. A. (1995). Inhibition of glycogen synthase kinase-3 by insulin mediated by protein kinase B. Nature 378, 785-9.

Cross, D. A., Alessi, D. R., Vandenheede, J. R., McDowell, H. E., Hundal, H. S., and Cohen, P. (1994). The inhibition of glycogen synthase kinase-3 by insulin or insulin-like growth factor 1 in the rat skeletal muscle cell line L6 is blocked by wortmannin, but not by rapamycin: evidence that wortmannin blocks activation of the mitogen-activated protein kinase pathway in L6 cells between Ras and Raf. Biochem J 303, 21-6.

Duff, K., Eckman, C., Zehr, C., Yu, X., Prada, C. M., Perez-tur, J., Hutton, M., Buee, L., Harigaya, Y., Yager, D., Morgan, D., Gordon, M. N., Holcomb, L., Refolo, L., Zenk, B., Hardy, J., and Younkin, S. (1996). Increased amyloid-beta42(43) in brains of mice expressing mutant presenilin 1. Nature 383, 710-3.

Estus, S., Tucker, H. M., van Rooyen, C., Wright, S., Brigham, E. F., Wogulis, M., and Rydel, R. E. (1997). Aggregated amyloid-beta protein induces cortical neuronal apoptosis and concomitant "apoptotic" pattern of gene induction. J Neurosci 17,7736-45.

Ferreira, A., Lu, Q., Orecchio, L., and Kosik, K. S. (1997). Selective phosphorylation of adult tau isoforms in mature hippocampal neurons exposed to fibrillar A beta. Mol Cell Neurosci 9,220-34.

Forloni, G., Chiesa, R., Smiroldo, S., Verga, L., Salmona, M., Tagliavini, F., and Angeretti, N. (1993). Apoptosis mediated neurotoxicity induced by chronic application of beta amyloid fragment 25-35. Neuroreport 4, 523-6.

Geula, C., Wu, C. K., Saroff, D., Lorenzo, A., Yuan, M., and Yankner, B. A. (1998). Aging renders the brain vulnerable to amyloid beta-protein neurotoxicity [see comments]. Nat Med 4, 827-31.

Gingrich, J. R., and Roder, J. (1998). Inducible gene expression in the nervous system of transgenic mice. Annu Rev Neurosci 21, 377-405.

Glenner, G. G., and Wong, C. W. (1984). Alzheimer's disease: initial report of the purification and characterization of a novel cerebrovascular amyloid protein. Biochem Biophys Res Commun 120, 885-90.1

Goedert, M., Spillantini, M. G., Potier, M. C., Ulrich, I., and Crowther, R. A. (1989). Cloning and sequencing of the cDNA encoding an isoform of microtubule-associated protein tau containing four tandem repeats: differential expression of tau protein mRNAs in human brain. Embo 18, 393-9.

Gomez-Isla, T., Hollister, R., West, H., Mui, S., Growdon, I. H., Petersen, R. C., Parisi, I. E., and Hyman, B. T. (1997). Neuronal-loss correlates with but exceeds neurofibrillary tangles in Alzheimer's disease. Ann Neurol 41, 17-24.

Gossen, M., and Bujard, H. (1992). Tight control of gene expression in mammalian cells by tetracycline-responsive promoters. Proc Natl Acad Sci USA 89, 5547-51.

Gotz, J., Probst, A., Spillantini, M. G., Schafer, T., lakes, R., Burki, K., and Goedert, M. (1995). Somatodendritic localization and hyperphosphorylation of tau protein in transgenic mice expressing the longest human brain tau isoform. Embo J 14, 1304-13.

Gray, E. G., Paula-Barbosa, M., and Roher, A. (1987). Alzheimer's disease: paired helical filaments and cytomembranes. Neuropathol Appl N eurobiol 13, 91-110.

Greenberg, S. G., Davies, P., Schein, I. D., and Binder, L. I. (1992). Hydrofluoric acid-treated tau PHF proteins display the same biochemical properties as normal tau. J Biol Chem 267, 564-9.

Grundke-Iqbal, I., Iqbal, K., Tung, Y. C., Quinlan, M., Wisniewski, H. M., and Binder, L. I. (1986). Abnormal phosphorylation of the microtubule-associated protein tau (tau) in Alzheimer cytoskeletal pathology. Proc Natl Acad Sci USA 83, 4913-7.

Guenette, S. Y., and Tanzi, R. E. (1999). Progress toward valid transgenic mouse models for Alzheimer's disease. Neurobiol Aging 20, 201-11.

Hall, A. C., Lucas, F. R., and Salinas, P. C. (2000). Axonal remodeling and synaptic differentiation in the cerebellum is regulated by WNT-7a signaling [In Process Citation]. Cell 100, 525-35.

Hardy, I. (1996). New insights into the genetics of Alzheimer's disease. Ann Med 28, 255-8.

Hetman, M., Cavanaugh, I. E., Kimelman, D., and Xia, z. (2000). Role of Glycogen Synthase Kinase-3beta in. Neuronal Apoptosis Induced by Trophic Withdrawal. J Neurosci 20, 2567-2574.

Hong, M., Chen, D. C., Klein, P. S., and Lee, V. M. (1997). Lithium reduces tau phosphorylation by inhibition of glycogen synthase kinase-3. J Biol Chem 272, 25326-32.

Hurel, S. J., Rochford, J. J., Borthwick, A. C., Wells, A. M., Vandenheede, J. R. Tumbull, D. M., and Yeaman, S. J. (1996). Insulin action in cultured human myoblasts: contribution of different signalling pathways to regulation of glycogen synthesis. Biochem J 320, 871-7.

Ishiguro, K., Ihara, Y., Uchida, T., and Imahori, K. (1988). A novel tubulin-dependent protein kinase forming a paired helical filament epitope on tau. J Biochem (Tokyo) 104, 319-21.

Ishihara, T., Hong, M., Zhang, B., Nakagawa, Y., Lee, M. K., Trojanowski, J. Q., and Lee, V. M. (1999). Age-dependent emergence and progression of a tauopathy in transgenic mice overexpressing the shortest human tau isoform. Neuron 24, 751-62.

Kelz, M. B., Chen, J., Carlezon, W. A., Jr., Whisler, K., Gilden, L., Beckmann, A. M., Steffen, C., Zhang, Y. J., Marotti, L., Self, D. W., Tkatch, T., Baranauskas, G., Surmeier, D. J., Neve, R. L., Duman, R. S., Picciotto, M. R., and Nestler, E. J. (1999). Expression of the transcription factor deltaFosB in the brain controls sensitivity to cocaine. Nature 401, 272-6.

Klein, P. S., and Melton, D. A. (1996). A molecular mechanism for the effect of lithium on development. Proc. Natl. Acad. Sci. USA 93,8455-8459.

Lee, V. M., Balin, B. J., Otvos, L., Jr., and Trojanowski, J. Q. (1991). A68: a major subunit of paired helical filaments and derivatized forms of normal Tau. Science 251, 675-8.

Loo, D. T., Copani, A., Pike, C. J., Whittemore, E. R., Walencewicz, A. J., and Cotman, C. W. (1993). Apoptosis is induced by beta-amyloid in cultured central nervous system neurons. Proc Natl Acad Sci USA 90,7951-5.

Lovestone, S., Hartley, C. L., Pearce, J., and Anderton, B. H. (1996). Phosphorylation of tau by glycogen synthase kinase-3 beta in intact mammalian cells: the effects on the organization and stability of microtubules. Neuroscience 73, 1145-57.

Lovestone, S., and Reynolds, C. H. (1997). The phosphorylation of tau: a critical stage in neurodevelopment and neurodegenerative processes. Neuroscience 78, 309-24.

Lovestone, S., Reynolds, C. H., Latimer, D., Davis, D. R., Anderton, B. H., Gallo, J. M., Hanger, D., Mulot, S., Marquardt, B., Stabel, S., and et at. (1994). Alzheimer's disease-like phosphorylation of the microtubule-associated protein tau by glycogen synthase: kinase-3 in transfected mammalian cells. Curr Biol 4, 1077-86.

Lucas, F. R., and Salinas, P. C. (1997). WNT-7a induces axonal remodeling and increases synapsin I levels in cerebellar neurons. Dev Biol 192, 31-44.

Manji, H. K., Moore, G. J., and Chen, G. (1999). Lithium at 50: have the neuroprotective effects of this unique cation been overlooked? Biol Psychiatry 46, 929-40.

Masters, C. L., Simms, G., Weinman, N. A., Multhaup, G., McDonald, B. L., and Beyreuther, K. (1985). Amyloid plaque core protein in Alzheimer disease and Down syndrome. Proc Natl Acad Sci USA 82,4245-9.

Mayford, M., Bach, M. E., Ruang, Y. Y., Wang, L., Rawkins, R. D., and Kandel, E. R. (1996). Control of memory formation through regulated expression of a CaMKII transgene. Science 274, 1678-83.

Metuzals, J., Robitaille, Y., Roughton, S., Gauthier, S., Kang, C. Y., and Leblanc, R. (1988). Neuronal transformations in Alzheimer's disease. Cell Tissue Res 252,239-48.

Morishima-Kawashima, M., Rasegawa, M., Takio, K., Suzuki, M., Yoshida, R., Titani, K., and Ihara, Y. (1995). Proline-directed and non-proline-directed phosphorylation of PHF-tau. J Biol Chem 270, 823-9.

Munoz-Montano, J. R., Moreno, F. J., Avila, J., and Diaz-Nido, J. (1997). Lithium inhibits Alzheimer's disease-like tau protein phosphorylation in neurons. FEBS Lett 411, 183-8.

Murayama, M., Tanaka, S., Palacino, J., Murayama, O., Ronda, T., Sun, X., Yasutake, K., Nihonmatsu, N., Wolozin, B., and Takashima, A. (1998). Direct association of presenilin-1 with beta-catenin. FEBS Lett 433, 73-7.

Nelson, P. T., Marton, L., and Saper, C. B. (1993). Alz-50 immunohistochemistry in the normal sheep striatum: a light and electron microscope study. Brain Res 600, 285-97.

Novak, M., lakes, R., Edwards, P. C., Milstein, C., and Wischik, C. M. (1991). Difference between the tau protein of Alzheimer paired helical filament core and normal tau revealed by epitope analysis of monoclonal antibodies 423 and 7.51. Proc Natl Acad Sci USA 88, 5837-41.

Otvos, L., Jr., Feiner, L., Lang, E., Szendrei, G. I., Goedert, M., and Lee, V. M. (1994). Monoclonal antibody PHF-1 recognizes tau protein phosphorylated at serine residues 396 and 404. J Neurosci Res 39, 669-73.

Pap, M., and Cooper, G. M. (1998). Role of glycogen synthase kinase-3 in the phosphatidylinositol 3-Kinase/Akt cell survival pathway. J Biol Chem 273, 19929-32.

Papasozomenos, S. C. (1989). Tau protein immunoreactivity in dementia of the Alzheimer type: II. Electron microscopy and pathogenetic implications. Effects of fixation on the morphology of the Alzheimer's abnormal filaments. Lab Invest 60, 375-89.

Pei, J. J., Braak, E., Braak, R., Grundke-Iqbal, I., Iqbal, K., Winblad, B., and Cowburn, R. F. (1999). Distribution of active glycogen synthase kinase 3beta (GSK-3beta) in brains staged for Alzheimer disease neurofibrillary changes. J Neuropathol Exp Neurol 58, 1010-9.

Pike, C. J., Walencewicz, A. J., Glabe, C. G., and Cotman, C. W. (1991). In vitro aging of beta-amyloid protein caus~s peptide aggregation and neurotoxicity. Brain Res 563, 311-4.

Price, D. L., and Sisodia, S. S. (1998). Mutant genes in familial Alzheimer's disease and transgenic models. Annu Rev Neurosci 21, 479-505.

Ruel, L., Bourouis, M., Heitzler, P., Pantesco, V., and Simpson, P. (1993). Drosophila shaggy kinase and rat glycogen synthase kinase-3 have conserved activities and act downstream of Notch. Nature 362, 557-60.

Saito, Y., Vandenheede, J. R., and Cohen, P. (1994). The mechanism by which epidermal growth factor inhibits glycogen synthase kinase 3 in A431 cells. Biochem J 303, 27-31.

Sanchez, S., Sayas, L., Lim, F., Diaz-Nido, J., Avila, J., and Wandosell, F. (2000). The inhibition of PI3-K induces neurite rectraction and activates GSK-3b. submitted.

Scheuner, D., Eckman, C., Jensen, M., Song, X., Citron, M., Suzuki, N., Bird, T. D., Hardy, J., Hutton, M., Kukull, W., Larson, E., Levy-Lahad, E., Viitanen, M., Peskind, E., Poorkaj, P., Schellenberg, G., Tanzi, R., Wasco, W., Lannfelt, L., Selkoe, D., and Younkin, S. (1996). Secreted amyloid beta-protein similar to that in the senile plaques of Alzheimer's disease is increased in vivo by the presenilin 1 and 2 and APP mutations linked to familial Alzheimer's disease [see comments]. Nat Med 2, 864-70.

Selkoe, D. J. (1998). The cell biology of beta-amyloid precursor protein and presenilin in Alzheimer's disease. Trends Cell Bio 18, 447-53.

Selkoe, D. J. (1994). Normal and abnormal biology of the beta-amyloid precursor protein. Annu Rev Neurosci 17, 489-517.

Seubert, P., Mawal-Dewan, M., Barbour, R., Jakes, R., Goedert, M., Johnson, G. V., Litersky, J. M., Schenk, D., Lieberburg, I., Trojanowski, J. Q., and et al. (1995). Detection of phosphorylated Ser262 in fetal tau, adult tau, and paired helical filament tau. J Biol Chem 270, 18917-22.

Shiurba, R. A., Ishiguro, K., Takahashi, M., Sato, K., Spooner, E. T., Mercken, M., Yoshida, R., Wheelock, T. R., Yanagawa, H., Imahori, K., and Nixon, R. A. (1996). Immunocytochemistry of tau phosphoserine 413 and tau protein kinase I in Alzheimer pathology. Brain Res 737, 119-32.

Siegfried, E., Chou, T. B., and Perrimon, N. (1992). Wingless signaling acts through zeste-white 3, the Drosophila homolog of glycogen synthase kinase-3, to regulate engrailed and establish cell fate. Cell 71, 1167-79.

Siegfried, E., Wilder, E. L., and Perrimon, N. (1994). Components of wingless signalling in Drosophila. Nature 367, 76-80.

Spittaels, K., Van den Haute, C., Van Dorpe, J., Bruynseels, K., Vandezande, K., Laenen, I., Geerts, H., Mercken, M., Sciot, R., Van Lommel, A., Loos, R., and Van Leuven, F. (1999). Prominent axonopathy in the brain and spinal cord of transgenic mice overexpressing four-repeat human tau protein. Am J Pathol 155, 2153-65.

Stambolic, V., Ruel, L., and Woodgett, J. R. (1996). Lithium inhibits glycogen synthase kinase-3 activity and mimics wingless signalling in intact cells [published erratum appears in Curr Biol Mar. 1, 1997;7(3):196]. Curr Biol 6, 1664-8.

Takashima, A., Honda, T., Yasutake, K., Michel, G., Murayama, O., Murayama, M., Ishiguro, K., and Yamaguchi, H. (1998). Activation of tau protein kinase I/glycogen synthase kinase-3beta by amyloid beta peptide (25-35) enhances phosphorylation of tau in hippocampal neurons. Neurosci Res 31, 317-23.

Takashima, A., Murayama, M., Murayama, O., Kohno, T., Honda, T., Yasutake, K., Nihonmatsu, N., Mercken, M., Yamaguchi, H., Sugihara, S., and Wolozin, B. (1998). Presenilin 1 associates with glycogen synthase kinase-3beta and its substrate tau. Proc Natl Acad Sci USA 95, 9637-41.

Takashima, A., Noguchi, K., Michel, G., Mercken, M., Hoshi, M., Ishiguro, K., and Imahori, K. (1996). Exposure of rat hippocampal neurons to amyloid beta peptide (25-35) induces the inactivation of phosphatidyl inositol-3 kinase and the activation of tau protein kinase I/glycogen synthase kinase-3 beta. Neurosci Lett 203, 33-6.

Takashima, A., Noguchi, K., Sato, K., Hoshino, T., and Imahori, K. (1993). Tau protein kinase I is essential for amyloid beta-protein-induced neurotoxicity. Proc Natl Acad Sci USA 90, 7789-93.

Terry, R. D. (1998). The cytoskeleton in Alzheimer disease. I Neural Transm Suppl 53, 141-5.

Weihl, C. C., Ghadge, G. D., Kennedy, S. G., Hay, N., Miller, R. J., and Roos, R. P. (1999). Mutant presenilin-1 induces apoptosis and downregulates Akt/PKB. J Neurosci 19, 5360-9.

Woodgett, J. R. (1990). Molecular cloning and expression of glycogen synthase kinase-3/factor A. Embo I9, 2431-8.

Yamamoto, A., Lucas, J. J., and Hen, R. (2000). Reversal of neuropathology and motor dysfunction in a conditional model of huntington's disease. Cell 101, 57-66.

Yankner, B. A. (1996). Mechanisms of neuronal degeneration in Alzheimer's disease. Neuron 16, 921-32.

Yu, G., Chen, F., Levesque, G., Nishimura, M., Zhang, D. M., Levesque, L., Rogaeva, E., Xu, D., Liang, Y., Duthie, M., St George-Hyslop, P. H., and Fraser, P. E. (1998). The presenilin 1 protein is a component of a high molecular weight intracellular complex that contains beta-catenin. I Biol Chem 273, 16470-5.

Zhang, Z., Hartmann, H., Do, V. M., Abramowski, D., SturcWer-Pierrat, C., Staufenbiel, M., Sommer, B., van de Wetering, M., Clevers, H., Saftig, P., De Strooper, B., He, X., and Yankner, B. A. (1998). Destabilization of beta-catenin by mutations in presenilin-1 potentiates neuronal apoptosis. Nature 395, 698-702.

The invention claimed is:

1. A transgenic mouse whose genome comprises a transgene comprising a DNA sequence encoding glycogen synthase kinase-3β (GSK-3β) operably linked to a tet-regulatable promoter and genome of the mouse further comprising a tetracycline-regulated transactivator (tTA) transgene, wherein GSK-3β protein is over-expressed in the mouse and the mouse develops neurodegeneration.

2. The transgenic mouse of claim 1, wherein GSK-3β is the only enzyme which is over-expressed.

3. The transgenic mouse of claim 1, wherein GSK-3β is the only protein which is over-expressed.

4. A method of identification of a therapy useful in the treatment of Alzheimer's disease, comprising administering the therapy to the transgenic mouse of claim 1 and monitoring the mouse for an effect on pathology or behavior.

5. The transgenic mouse of claim 1, wherein the tTA transgene is under control of a CamKIIα promoter.

6. The transgenic mouse of claim 1, wherein overexpression of GSK-3β is found in the hippocampus and cortex, but not in the striatum.

7. A method of testing a drug or therapy to treat a neurodegenerative disease, comprising administering the drug or therapy to a transgenic mouse of claim 1, and monitoring the transgenic mouse for an effect on pathology or behavior.

8. A method of making a transgenic mouse over-expressing GSK-3β, comprising introducing a transgene comprising a DNA sequence encoding glycogen synthase kinase-3β (GSK-3β) operably linked to a tet-regulatable promoter into a mouse oocyte, and crossing a resulting mouse whose genome comprises the transgene with a mouse whose genome comprises a tTA transgene to produce a transgenic mouse of claim 1.

* * * * *